United States Patent
Sutariya et al.

(10) Patent No.: US 11,998,562 B2
(45) Date of Patent: Jun. 4, 2024

(54) OPHTHALMOLOGICAL FORMULATIONS FOR THE PREVENTION OF A CORONAVIRUS INFECTION

(71) Applicant: UNIVERSITY OF SOUTH FLORIDA, Tampa, FL (US)

(72) Inventors: Vijaykumar Sutariya, Tampa, FL (US); Srinivas Tipparaju, Tampa, FL (US); Kevin Sneed, Tampa, FL (US); Manas Biswal, Tampa, FL (US); Ramesh Ayyala, Tampa, FL (US); Radouil Tzekov, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/583,781

(22) Filed: Jan. 25, 2022

(65) Prior Publication Data
US 2022/0233564 A1  Jul. 28, 2022

Related U.S. Application Data

(60) Provisional application No. 63/141,366, filed on Jan. 25, 2021.

(51) Int. Cl.
*A61K 31/706* (2006.01)
*A61K 9/00* (2006.01)
*A61K 31/573* (2006.01)

(52) U.S. Cl.
CPC .......... *A61K 31/706* (2013.01); *A61K 9/0048* (2013.01); *A61K 31/573* (2013.01)

(58) Field of Classification Search
None
See application file for complete search history.

(56) References Cited

U.S. PATENT DOCUMENTS

| | | | |
|---|---|---|---|
| 11,020,349 B1 * | 6/2021 | Nandi | A61K 9/2018 |
| 2005/0048099 A1 * | 3/2005 | Shiah | A61P 9/10 424/428 |
| 2018/0147297 A1 * | 5/2018 | Loftsson | A61K 47/34 |
| 2019/0255085 A1 | 8/2019 | Clarke et al. | |

FOREIGN PATENT DOCUMENTS

| | | |
|---|---|---|
| WO | 2013125977 | 8/2013 |
| WO | 2016069826 | 5/2016 |
| WO | 2019079339 | 4/2019 |

OTHER PUBLICATIONS

Napoli, P. E., Mangoni, L., Gentile, P., Braghiroli, M., & Fossarello, M. (2020). A panel of broad-spectrum antivirals in topical ophthalmic medications from the drug repurposing approach during and after the coronavirus disease 2019 era. Journal of Clinical Medicine, 9(8), 2441. (Year: 2020).*

Sahu, D. K., Pradhan, D., Naik, P. K., Kar, B., Ghosh, G., & Rath, G. (2020). Smart polymeric eye gear: A possible preventive measure against ocular transmission of COVID-19. Medical Hypotheses, 144, 110288. (Year: 2020).*

Shetty R, Ghosh A, Honavar SG, Khamar P, Sethu S. Therapeutic opportunities to manage COVID-19/SARS-COV-2 infection: Present and future. Indian J Ophthalmol [serial online] 2020 [cited May 22, 2020];68:693-702. Available from: http://www.ijo.in/text.asp?2020/68/5/693/281523.

Sheahan, Timothy P., et al. "Broad-spectrum antiviral GS-5734 inhibits both epidemic and zoonotic coronaviruses." Science translational medicine 9.396 (2017): eaal3653.

Wang, Manli, et al. "Remdesivir and chloroquine effectively inhibit the recently emerged novel coronavirus (2019-nCOV) in vitro." Cell research 30.3 (2020): 269-271.

Eye Care During COVID-19: Masks, Vaccines and Procedures, by Reena Mukamal; Edited by Anni Delfaro May 18, 2021 https://www.aao.org/eye-health/tips-prevention/coronavirus-covid19-eye-infection-pinkeye.

Ayaki, Masahiko, Atsuo Iwasawa, and Yoshimi Niwano. "Comparative assessment of the cytotoxicity of six anti-inflammatory eyedrops in four cultured ocular surface cell lines, as determined by cell viability scores." Clinical Ophthalmology (Auckland, NZ) 6 (2012): 1879-1884.

Gralinski, Lisa E., and Ralph S. Baric. "Molecular pathology of emerging coronavirus infections." The Journal of pathology 235.2 (2015): 185-195.

* cited by examiner

*Primary Examiner* — Dale R Miller
(74) *Attorney, Agent, or Firm* — Meunier Carlin & Curfman LLC

(57) ABSTRACT

The present disclosure provides for an ophthalmological composition comprising remdesivir and an ophthalmologically suitable carrier, and the use thereof for treating and preventing a coronavirus infection and treating conjunctivitis.

18 Claims, 3 Drawing Sheets

OPHTHALMOLOGICAL FORMULATIONS FOR THE PREVENTION OF A CORONAVIRUS INFECTION

CROSS-REFERENCE TO RELATED APPLICATIONS

The application claims the benefit of priority to U.S. Provisional Application No. 63/141,366, filed Jan. 25, 2021, the disclosure of which is incorporated herein by reference in its entirety.

BACKGROUND

Remdesivir is a therapeutic option for patients with COVID-19. Remdesivir is an investigational intravenous drug with broad antiviral activity that inhibits viral replication through premature termination RNA transcription and has in vitro activity against SARS-CoV-2 and in vitro and in vivo activity against related beta-coronaviruses. It has demonstrated in vitro and in vivo activity in animal models against the viral pathogens that cause Mideast Respiratory Syndrome (MERS) and Sever Acute Respiratory Syndrome (SARS), both of which are coronaviruses structurally similar to SARS-CoV-2, the coronavirus that causes COVID-19. Studies have also shown that individuals hospitalized with coronavirus may experience viral pink eye, otherwise known as conjunctivitis. The virus can spread by touching fluid from an infected person's eyes, or from objects that carry the fluid. Therefore, there would be significant benefits to preventing transmission of the coronavirus via an infected person's eye and treating conjunctivitis caused by the coronavirus. Antiviral therapeutic strategies and multimodal ways of blocking entry of the virus into blood circulation decrease transmission of coronavirus via ocular secretions and direct or indirect contact.

The compositions and methods disclosed herein address these and other needs.

SUMMARY

The present disclosure provides compositions that can be useful in preventing a coronavirus infection and treating conjunctivitis caused by coronavirus, e.g., SARS-CoV-2. Further, the present disclosure provides methods of preventing and treating a coronavirus infection in a subject, and treating conjunctivitis caused by coronavirus, e.g., SARS-CoV-2.

Thus, in one aspect, an ophthalmological composition is provided including remdesivir and an ophthalmologically suitable carrier.

In another aspect, methods of preventing a coronavirus infection in an eye of a subject are provided including administering to the subject a therapeutically effective amount of an ophthalmological composition as described herein.

In a further aspect, methods of treating conjunctivitis in an eye of a subject are provided including administering to the subject a therapeutically effective amount of an ophthalmological composition as described herein.

In another aspect, methods of treating a coronavirus infection in a subject are provided including administering to the subject a therapeutically effective amount of an ophthalmological composition as described herein.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
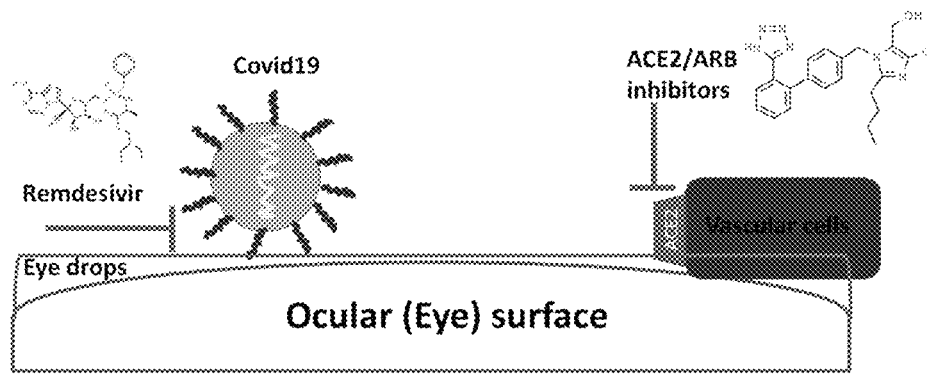
FIG. 1 shows an outline and concept for ocular drug delivery of Remdesivir and ARB's (angiotensin receptor blockers). ACE2 (angiotensin converting enzyme).
Figure 2:
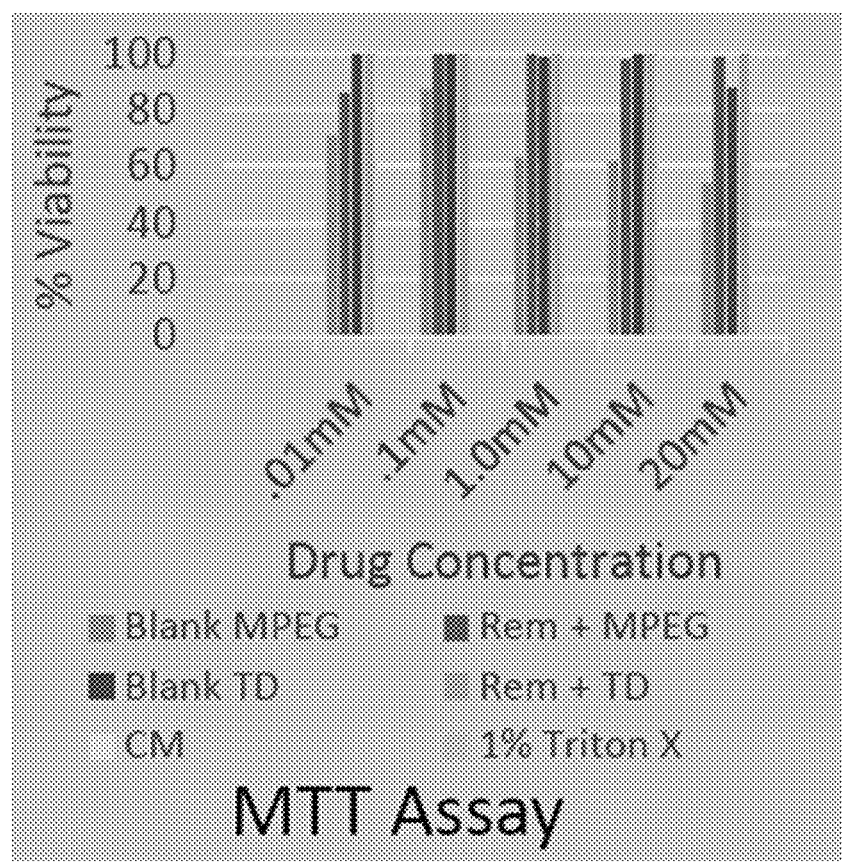
FIG. 2 shows a graph of percent viability versus drug concentration.
Figure 3:
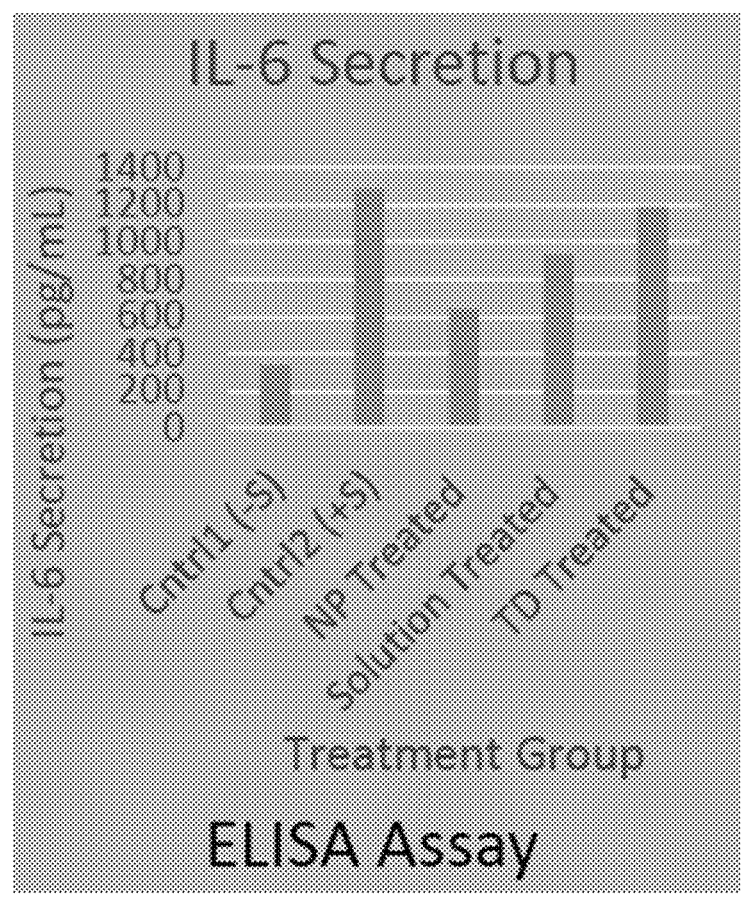
FIG. 3 shows a graph of IL-6 secretion (pg/mL) per treatment group.
Figure 4:
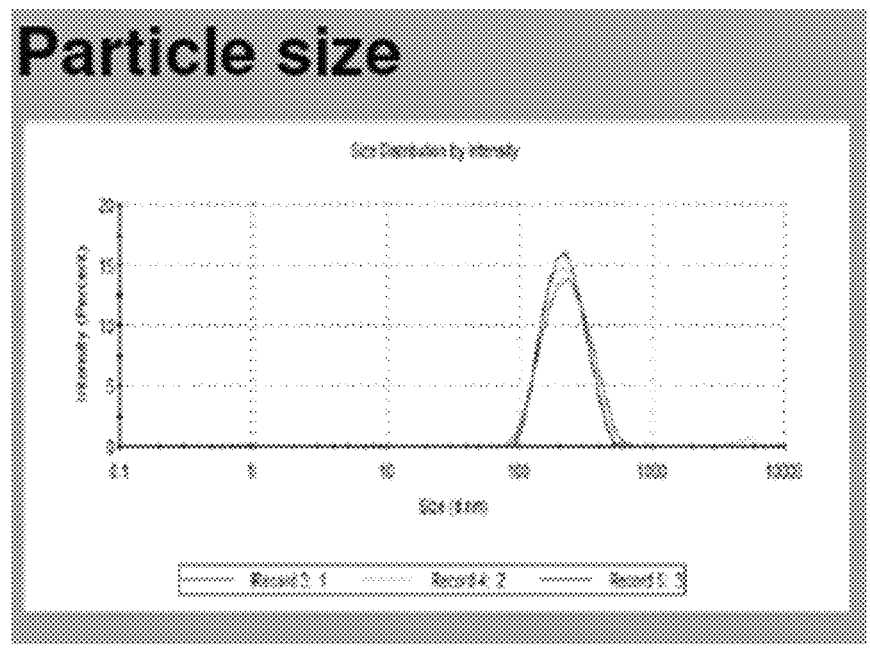
FIG. 4 shows remdesivir micelle formulation size distribution as averaged by dynamic light scattering measurement.
Figure 5:
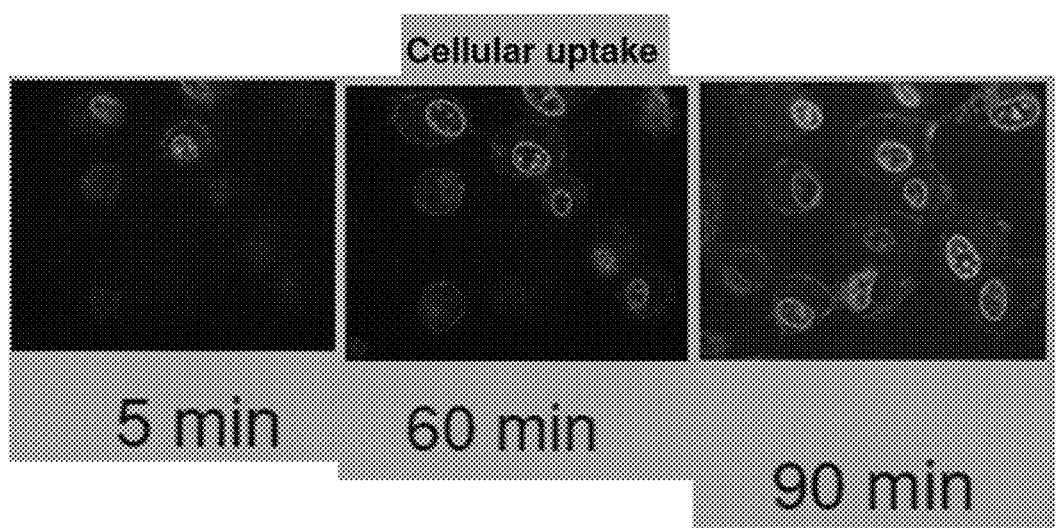
FIG. 5 shows confocal microscopy images of ARPE-19 cells treated with NBD (fluorescent green) cholesterol loaded micelles. Remdesivir nanomicelles (NP) uptake was analyzed at different time points (5A) 5 minutes, (5B) 60 minutes, and (5C) 90 minutes.

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound or composition can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms. As used herein, the term "preventing" a disorder or unwanted physiological event in a subject refers specifically to the prevention of the occurrence of symptoms and/or their underlying cause, wherein the subject may or may not exhibit heightened susceptibility to the disorder or event. In particular embodiments, "prevention" includes reduction in risk of coronavirus infection in patients. However, it will be appreciated that such prevention may not be absolute, i.e., it may not prevent all such patients developing a coronavirus infection, or may only partially prevent an infection in a single individual. As such, the terms "prevention" and "prophylaxis" may be used interchangeably.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used interchangeably herein, "subject," "individual," or "patient" can refer to a vertebrate organism, such as a mammal (e.g., human) "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as glaucoma. The effect can be therapeutic in terms of a partial or complete cure of a disease, condition, symptom or adverse effect attributed to the disease, disorder, or condition. The term "treatment" as used herein can include any treatment of a disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating" can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

As used herein, the term "remdesivir" is used in broad sense to include not only "remdesivir" per se (free base) but also its pharmaceutically acceptable salts, solvates, esters, hydrates, isomers, enantiomers, stereoisomers, diastereoisomers, derivatives, metabolites, polymorphs and prodrugs thereof. Polymorph may refer to various crystalline and amorphous forms, which can be characterized by methods such as melting point, X-ray diffraction pattern, Raman spectra, IR spectra or any other method known in the art.

Ophthalmological Composition

The present disclosure provides for an ophthalmological composition including remdesivir or pharmaceutically acceptable salts thereof and an ophthalmologically suitable carrier.

Remdesivir is a single stereoisomer monophosphoramidate prodrug of a nucleoside analog, that is being developed for the treatment of coronavirus disease. Remdesivir is chemically known as 2-Ethylbutyl (2S)-2-{[(S)-{[(2R,3S, 4R,5R)-5-(4-aminopyrrolo[2,1-f][1,2,4]triazin-7-yl)-5-cyano-3,4-dihydroxytetrahydrofuran-2-yl]methoxy}(phenoxy)phosphoryl]amino}propanoate. Remdesivir is a white to off-white or yellow non-hygroscopic solid. It is practically insoluble in water and is represented by the following formula as:

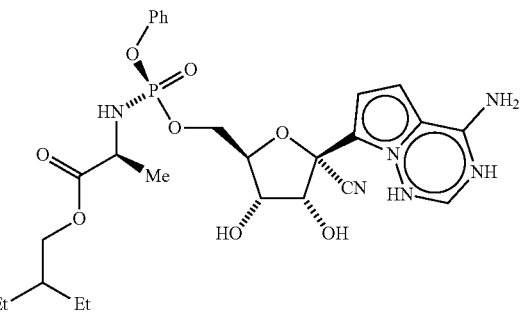

Remdesivir is a prodrug that metabolizes into its active form GS-441524. GS-441524 is an adenosine nucleotide analog that interferes with the action of viral RNA polymerase and evades proofreading by viral exoribonuclease, causing a decrease in viral RNA production.

Remdesivir is presently approved in many countries in the form of an injectable dosage form in the strength of 100 mg by Gilead Sciences for the treatment of infection caused by coronavirus disease 2019 (COVID-19). Remdesivir is reported to be poorly water soluble, which leads to poor dissolution and poor bioavailability. Moreover, remdesivir is not a first choice for oral delivery as its shows poor hepatic stability, which results in its complete first-pass clearance. These characteristics of remdesivir pose technical challenges to formulation scientists in the development of a suitable oral formulation with desired technical attributes.

PCT Patent Publication No. WO2016/069826 assigned to Gilead Sciences discloses remdesivir as compound. This patent publication also discloses use of remdesivir in the treatment of Filoviridae infection. The publication provides a listing of numerous dosage forms and excipients that may be included in the dosage form along with the numerous compounds disclosed. US Patent Publication No. US2019/0255085 assigned to Gilead Sciences discloses use of remdesivir in the treatment of Coronaviridae infection in a human. The publication provides a listing of numerous dosage forms and excipients that may be included in the dosage form with the various compounds disclosed.

The ophthalmological composition disclosed herein can include an ophthalmologically acceptable carrier. As used herein, an "ophthalmologically acceptable carrier" refers to an ophthalmologically acceptable solvent, suspending agent or vehicle for delivering remdesivir to the eye of a subject. The carrier may be solid or liquid. The carrier is "ophthalmologically acceptable" in that the carrier is suitable for administering to the eye without causing any or a substantial adverse reaction. The ophthalmologically acceptable carrier may include water. In some embodiments, the formulation can include greater than 50 wt % (e.g., greater than 60 wt %, 65 wt %, 70 wt %, 75 wt %, 80 wt %, 85 wt %, or 90 wt %), more typically greater than 95 wt %, water (e.g. 96 wt %, 97 wt %, 98 wt %, or 99 wt %). In some embodiments, the ophthalmologically acceptable carrier may be an oil-in-water emulsion, or an oil. In such embodiments, the ophthalmic formulation may be in the form of a cream for application to the eye. In such embodiments, the formulation may comprise greater than 10 wt %, more typically greater than 20 wt %, of an oleaginous ingredient. In other embodiments, the carrier can be a biodegradable polymer, for example, for a biodegradable polymer ocular insert for extended release of the compound of remdesivir and optionally other compounds.

In some embodiments, the carrier can include an excipient. Excipients suitable for use may include, for example, demulcents, emollients, hypertonicity agents, preservatives, buffers or pH adjusting agents. In further embodiments, demulcents may include, but are not limited to, synthetic high molecular weight crosslinked polymers of acrylic acid (e.g. Carbomer 974 and Carbomer 980), cellulose derivatives (e.g. hydroxypropyl methylcellulose ("HPMC" or "hypromellose"), hydroxyethylcellulose, methylcellulose, carboxymethylcellulose (carmellose) or sodium carboxymethylcellulose (sodium carmellose)), dextran (e.g. Dextran 70), gelatin, polyols (e.g. as glycerin, polyethylene glycol 300, polyethylene glycol 400, polysorbate 80, and propylene glycol), polyvinyl alcohol, povidone (polyvinylpyrrolidone), poloxamer, or hyaluronic acid (a polymer of disaccharides), or its sodium or potassium salt.

In some embodiments, emollients may include, but are not limited to, lanolins (e.g. anhydrous lanolin), oleaginous ingredients (e.g. light mineral oil, mineral oil, paraffin, petrolatum, white ointment, white petrolatum, white wax and yellow wax), or castor oil. In some embodiments, preservatives may include, but are not limited to, benzalkonium chloride, sodium perborate, Oxyd (sodium chlorite 0.05%, hydrogen peroxide 0.01%); polyquartemium-1 (ethanol, 2,2',2"-nitrilotris-, polymer with 1,4-dichloro-2-butene and N,N,N',N'tetramethyl-2-butene-1,4-diamine), sodium silver chloride, hexamethylene biguanide, oxyborate, or Purite™ (sodium chlorite 0.005% m/v).

In some embodiments, ophthalmic hypertonicity agents include, but are not limited to, sodium chloride.

In some embodiments, the carrier may contain liposomes incorporating the remdesivir, wherein liposomes are artificially prepared vesicles composed mainly of phospholipids. The vesicles may be suspended in aqueous solutions with high viscosity polymers (e.g., hydroxyethylcellulose, methylcellulose, hydroxypropylmethylcellulose) and vinylic derivatives (e.g., polyvinylpirrolidone, polyvinyl alcohol) and their mixtures. Neutral liposomes may be prepared from phosphatidylcholine associated with mucoadhesive polymers.

In particular embodiments, eye drops may include the ophthalmological composition. Eye drops may include, but are not limited to, aqueous ophthalmic solutions, aqueous ophthalmic suspensions, non-aqueous ophthalmic solutions and non-aqueous ophthalmic suspensions, gels, and ophthalmic ointments. In some embodiments, eye drops may include cyclodextrin. In further embodiments, the composition may comprise at least 10%, 15%, 20%, 25%, 30%, 35%, 40%, 45%, 50%, 55%, 60%, 65%, 70%, 75%, 80%, 85%, 90%, 95% or 99% cyclodextrin (the percentages are % w/v). Further, the cyclodextrin may comprise one or more of a beta-cyclodextrin, a gamma-cyclodextrin or an alpha-cyclodextrin. In other embodiments, the cyclodextrin comprises a modified or substituted cyclodextrin. For example, the cyclodextrin may comprise one or more substituents selected from hydroxypropyl (e.g., 2-hydroxypropyl), sulfobutyl and methyl. In certain embodiments, the cyclodextrin is a hydroxypropyl (beta-)cyclodextrin (e.g., Kleptose™ HPB), more particularly 2-hydroxypropyl (beta-)cyclodextrin. In particular embodiments, the cyclodextrin comprises a methyl-cyclodextrin, for example a randomly methylated beta-cyclodextrin. In certain embodiments, the cyclodextrin is a sulfobutylether cyclo-35 dextrin, for example a sulfobutylether beta-cyclodextrin (e.g., Captisol™).

In some embodiments, the eye drops may include one or more preservatives. In further embodiments, the preservative may include Thiomersal (i.e., sodium (2-carboxylatophenyl)sulfanyl-ethylmercury; also known as thimerosal). In further embodiments, the concentration of Thiomersal may be at least 0.005, 0.008, 0.01, 0.015 or 0.02% w/v Thiomersal. In particular embodiments, the composition comprises at least 0.01% w/v Thiomersal and at least 0.2% w/v remdesivir. In particular embodiments, the compositions according to the present invention further may comprise one or more buffering agents, such as a phosphate buffer like sodium phosphate. In certain embodiments, the compositions according to the present invention may further comprise one or more pH adjusting agents, such as sodium hydroxide, hydrochloric acid, or combinations thereof. It has been found by the present inventors that the use of cyclodextrin does not require the use of solubilizing agents with an elevated pH.

In certain embodiments, the compositions according to the present invention may further comprise one or more tonicity adjusting agents, for example selected from the group consisting of dextrose, glycerin, manitol, potassium chloride, sodium chloride and phosphate buffers. Tonicity adjusting agents can be used to modify the osmotic pressure or osmolarity of a composition. The skilled person will further understand that the compositions of the present invention are preferably sterile and devoid of exogenous particles. Thus, as indicated above, the compositions of the present invention may comprise, in addition to remdesivir and cyclodextrin, one or more preservatives and/or buffering agents. In some embodiments, the compositions of the present disclosure can include remdesivir, cyclodextrin, and an aqueous solution such as a buffer.

In some embodiments, the concentration of remdesivir in the ophthalmologically suitable carrier can be 0.001 wt % to 20 wt %, e.g., about 0.01 wt % to about 1 wt %, about 0.1 wt % to about 10 wt %, about 0.1 wt % to about 5 wt %, about 1 wt % to about 5 wt %, or about 2 wt % to about 4 wt %. For example, the compounds of formula (I) may be present in the ophthalmological composition in an amount of 0.001 wt %, 0.002 wt %, 0.003 wt %, 0.004 wt %, 0.005 wt %, 0.006 wt %, 0.007 wt %, 0.008 w t %, 0.009 wt %, 0.01 wt %, 0.02 wt %, 0.03 wt %, 0.04 wt %, 0.05 wt %, 0.06 wt %, 0.07 wt %, 0.08 wt %, 0.09 wt %, 0.1 wt %, 0.2 wt %, 0.3 wt %, 0.4 wt %, 0.5 wt %, 0.6 wt %, 0.7 wt %, 0.8 wt %, 0.9 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt %. In some embodiments, the ophthalmological composition can further include an angiotensin converting enzyme inhibitor (ACEI). In certain embodiments, the ACEI may include benazepril, captopril, enalaprilat, fosinopril, lisinopril, moexipril, perindopril, quinapril, ramipril, trandolapril, or any combination thereof.

In some embodiments, the ophthalmological composition may further include an angiotensin receptor blocker (ARB). In some embodiments, the ARB may include azilsartan, candesartan, eprosartan, irbesartan, olmesartan, valsartan, losartan, telmisartan, or any combination thereof. In certain embodiments, the ARB may include losartan, telmisartan, or any combination thereof.

In some embodiments, the ophthalmological composition may include a corticosteroid. As used herein, corticosteroid refers to any natural or synthetic compound characterized by a hydrogenated cyclopentanoperhydrophenanthrene ring system and having immunosuppressive and/or anti-inflammatory activity. In some embodiments, the corticosteroid is natural and produced in the adrenal cortex. In other embodiments, the corticosteroid may be synthetic. In further embodiments, the synthetic corticosteroids may be halogenated.

In further embodiments, the corticosteroid may include dexamethasone. In other embodiments, the corticosteroid may include be a synthetic corticosteroid including but not limited to prednisone, prednisolone, dexamethasone, dexamethasone triamcinolone, hydrocortisone, betamethasone, or any combination thereof.

In some embodiments, the ophthalmologically suitable carrier may include nanoparticles. In some embodiments, the ophthalmologically suitable carrier may include biodegradable polymer, a lipid, or any combination thereof. In some embodiments, the nanoparticles may encapsulate remdesivir.

In some embodiments, the nanoparticles may have an average diameter from 1 nm to 500 nm. In other embodiments, the nanoparticles may have an average diameter of from 150 nm to 300 nm, from 200 to 250 nm, from 100 nm to 250 nm, from 300 nm to 500 nm, from 350 nm to 500 nm, from 50 nm to 250 nm, from 1 nm to 100 nm, or from 1 nm to 300 nm.

In some embodiments, the nanoparticles may be formed by a biodegradable polymer, a lipid, or any combination thereof.

Suitable biodegradable polymer may include but are not limited to a poly(hydroxy acid); poly(lactic acid); poly(glycolic acid); poly(lactic acid-co-glycolic acid); poly(lactic-co-glycolic acid); a polyanhydride; a polyorthoester; a polyamide; a polycarbonate; a polyalkylene; polyethylene; polypropylene; a polyalkylene glycol; poly(ethylene glycol); methoxypoly(ethylene glycol); a polyalkylene oxide; poly(ethylene oxide); a polyalkylene terephthalate; poly(ethylene terephthalate); a polyvinyl alcohol; a polyvinyl ether; a polyvinyl ester; a polyvinyl halide; poly(vinyl chloride); polyvinylpyrrolidone; a polysiloxane; a poly(vinyl acetate); a polyurethane; a co-polymer of a polyurethane; a derivativized cellulose; alkyl cellulose; a hydroxyalkyl cellulose; a cellulose ether; a cellulose ester; a nitro cellulose; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; a polymer of acrylic acid; methacrylic acid; a copolymer of methacrylic acid; a derivative of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); a copolymer of poly(lactide-co-caprolactone); a blend of poly(lactide-co-caprolactone); polygalactia poly(isobutyl cyanoacrylate); poly(2-hydroxyethyl-L-glutamine); poly(caprolactone); or any combination, or copolymers thereof.

Suitable lipids can include but are not limited to naturally occurring, synthetic, or semi-synthetic molecules that include fats, waxes, sterols, fat-soluble vitamins (such as vitamins A, D, E, and K), monoglycerides, diglycerides, triglycerides, phospholipids, and others.

Lipids may be broadly defined as hydrophobic or amphiphilic small molecules; the amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups.

Lipids may be divided into eight categories: fatty acids, glycerolipids, glycerophospholipids, sphingolipids, saccharolipids, and polyketides (derived from condensation of ketoacyl subunits); and sterol lipids (e.g., cholesterol) and prenol lipids (derived from condensation of isoprene subunits).

Fatty acids, or fatty acid residues when they form part of a lipid, are a diverse group of molecules which can be prepared synthetically or synthesized naturally by chain-elongation of an acetyl-CoA primer with malonyl-CoA or methylmalonyl-CoA groups in a process called fatty acid synthesis. Fatty acids are made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. Where a double bond exists, there is the possibility of either a cis or trans geometric isomerism, which significantly affects the molecule's configuration. Cis-double bonds cause the fatty acid chain to bend, an effect that is compounded with more double bonds in the chain. Most naturally occurring fatty acids are of the cis configuration, although the trans-form does exist in some natural and partially hydrogenated fats and oils. Other major lipid classes in the fatty acid category are the fatty esters and fatty amides.

Glycerolipids are composed mainly of mono-, di-, and tri-substituted glycerols, the most well-known being the fatty acid triesters of glycerol, called triglycerides. The word "triacylglycerol" is sometimes used synonymously with "triglyceride", though the latter lipids contain no hydroxyl group. In these compounds, the three hydroxyl groups of glycerol are each esterified, typically by different fatty acids.

Additional subclasses of glycerolipids are represented by glycosylglycerols, which are characterized by the presence of one or more sugar residues attached to glycerol via a glycosidic linkage. Examples of structures in this category are the digalactosyldiacylglycerols found in plant membranes and seminolipid from mammalian sperm cells.

Glycerophospholipids, usually referred to as phospholipids, are ubiquitous in nature and are key components of the lipid bilayer of cells, as well as being involved in metabolism and cell signaling. Most phospholipids contain a diglyceride, a phosphate group, and a simple organic molecule such as choline; one exception to this rule is sphingomyelin, which is derived from sphingosine instead of glycerol.

The structure of the phospholipid molecule generally consists of hydrophobic tails and a hydrophilic head. The 'head' is attracted to water, while the hydrophobic 'tails' are repelled by water and are forced to aggregate. The hydrophilic head contains the negatively charged phosphate group and may contain other polar groups. The hydrophobic tail usually consists of long fatty acid hydrocarbon chains. When placed in water, phospholipids form a variety of structures depending on the specific properties of the phospholipid.

Lipid bilayers occur when hydrophobic tails line up against one another, forming a membrane of hydrophilic heads on both sides facing the water.

Glycerophospholipids may be subdivided into distinct classes, based on the nature of the polar headgroup at the sn-3 position of the glycerol backbone in eukaryotes and eubacteria, or the sn-1 position in the case of archaebacteria. Examples of glycerophospholipids found in biological membranes are phosphatidylcholine (also known as PC, GPCho or lecithin), phosphatidylethanolamine (PE or GPEtn) and phosphatidylserine (PS or GPSer).

In eukaryotes, phospholipids are generally classified into two types: diacylglycerides and phosphingolipids. Examples of diacylglycerides include, but are not limited to, phosphatidic acid (phosphatidate) (PA), phosphatidylethanolamine (cephalin) (PE), phosphatidylcholine (lecithin) (PC), phosphatidylserine (PS), and phosphoinositides, such as phosphatidylinositol (PI), phosphatidylinositol phosphate (PIP), phosphatidylinositol bisphosphate (PIP2) and, phosphatidylinositol triphosphate (PIPS). Examples of phospingolipids include, but are not limited to, ceramide phosphorylcholine (Sphingomyelin) (SPH), ceramide phosphoryl ethanolamine (Sphingomyelin) (Cer-PE), and Ceramide phosphoryllipid.

In some embodiments, the biodegradable polymer may comprise a poly(hydroxy acid); poly(lactic acid); poly(glycolic acid); poly(lactic acid-co-glycolic acid); poly(lactic-co-glycolic acid); a polyanhydride; a polyorthoester; a polyamide; a polycarbonate; a polyalkylene; polyethylene; polypropylene; a polyalkylene glycol; poly(ethylene glycol); methoxypoly(ethylene glycol); a polyalkylene oxide; poly(ethylene oxide); a polyalkylene terephthalate; poly (ethylene terephthalate); a polyvinyl alcohol; a polyvinyl ether; a polyvinyl ester; a polyvinyl halide; poly(vinyl chloride); polyvinylpyrrolidone; a polysiloxane; a poly(vinyl acetate); a polyurethane; a co-polymer of a polyurethane; a derivatized cellulose; alkyl cellulose; a hydroxyalkyl cellulose; a cellulose ether; a cellulose ester; a nitro cellulose; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; a polymer of acrylic acid; methacrylic acid; a copolymer of methacrylic acid; a derivative of methacrylic acid; poly(methyl methacrylate); poly(ethyl methacrylate); poly(butylmethacrylate); poly(isobutyl methacrylate); poly (hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); a copolymer of poly (lactide-co-caprolactone); a blend of poly(lactide-co-caprolactone); polygalactia poly-(isobutyl cyanoacrylate); poly(2-hydroxyethyl-L-glutamine); poly(caprolactone); or any combination, or copolymers thereof.

In some embodiments, the lipid may include fatty acids, glycerolipids, glycerophospholipids, sphingolipids, saccharolipids, polyketides, sterol lipids, prenol lipids, or any combination thereof.

In further embodiments, the biodegradable polymer may include methoxypoly(ethylene glycol), poly(caprolactone), or any combination thereof.

In some embodiments, the lipid is present in an amount of from 20 to 99 mole percent based on the composition. In some embodiments, the lipid may be present in an amount from about 25 to about 90 mole percent or in further embodiments, from about 25 to about 80 mole percent. In other embodiments, the concentration may be from about 40 to about 70 mole percent, preferably from about 40 to about 60 mole percent.

Methods of Use

Methods of Preventing of Coronavirus Infection

The present disclosure provides for a method of preventing of coronavirus infection in a subject including administering to the subject a therapeutically effective amount of an ophthalmological composition, as discussed herein. In some embodiments, the subject is human.

In certain embodiments, the method may include application of the ophthalmological composition to the (affected) eye two or three times per day. The optimal application frequency may depend on factors such as the severity of the infection and the concentration of remdesivir in the composition. In some embodiments, the composition is applied onto the (affected) eye two or three times per day, for at least one, two, three or four weeks. In certain embodiments, the treatment is continued 1, 2, 3, 4, 5, 6, 7, 8, 9, 10 or more days after disappearance of the clinical symptoms.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days. The active ingredient may be administered in such amounts, time, and route deemed necessary in order to achieve the desired result. The exact amount of the active ingredient will vary from subject to subject, depending on the species, age, and general condition of the subject, the severity of the medical disorder, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

Methods of Treating Conjunctivitis

Conjunctivitis is an inflammation or infection of the transparent membrane (conjunctiva) that lines the eyelid and covers the white part of the eyeball. When small blood vessels in the conjunctiva become inflamed, they are more visible, thus causing the whites of your eyes to appear reddish or pink. Conjunctivitis may be very contagious and may be spread through direct or indirect contact with the liquid that drains from the eye of the infected subject. One or both eyes may be affected.

The present disclosure provides for a method of treating conjunctivitis in an eye of a subject in need thereof including administering to the subject a therapeutically effective amount of an ophthalmological composition as described herein. In some embodiments, the subject is human.

In certain embodiments, the method may include application of the ophthalmological composition to the (affected) eye two or three times per day. The optimal application frequency may depend on factors such as the severity of the infection and the concentration of remdesivir in the composition. In some embodiments, the composition is applied onto the (affected) eye two or three times per day, for at least one, two, three or four weeks. In certain embodiments, the treatment is continued 1, 2, 3, 4, 5, 6, 7, 8, 9, 10 or more days after disappearance of the clinical symptoms.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days. The active ingredient may be administered in such amounts, time, and route deemed necessary in order to achieve the desired result. The exact amount of the active ingredient will vary from subject to subject, depending on the species, age, and general condition of the subject, the severity of the medical disorder, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

In some embodiments, conjunctivitis can be a viral infection. In some embodiments, conjunctivitis can occur along with a cold or symptoms of a respiratory infection, such as a sore throat. In certain embodiments, symptoms of conjunctivitis include redness in one or both eyes, itchiness in one or both eyes, a gritty feeling in one or both eyes, a discharge in one or both eyes that forms a crust during the night that may prevent your eye or eyes from opening in the morning, and/or tearing.

In some embodiments, conjunctivitis is caused by a coronavirus infection.

Methods of Inhibiting Coronavirus Spike Protein Interaction

The present disclosure provides for a method of inhibiting a coronavirus spike protein interaction with angiotensin converting enzyme II (ACE2) in the eye of a subject, the method including administering to a part of the eye of the subject an effective amount of an ophthalmic composition, as discussed herein. In some embodiments, the subject is human.

In certain embodiments, the method may include application of the ophthalmological composition to the (affected) eye two or three times per day. The optimal application frequency may depend on factors such as the severity of the infection and the concentration of remdesivir in the composition. In some embodiments, the composition is applied onto the (affected) eye two or three times per day, for at least one, two, three or four weeks. In certain embodiments, the treatment is continued 1, 2, 3, 4, 5, 6, 7, 8, 9, 10 or more days after disappearance of the clinical symptoms.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days. The active ingredient may be administered in such amounts, time, and route deemed necessary in order to achieve the desired result. The exact amount of the active ingredient will vary from subject to subject, depending on the species, age, and general condition of the subject, the severity of the medical disorder, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

In some embodiments, the methods can further include administering a corticosteroid, as described herein. In some embodiments, the corticosteroid can be dexamethasone.

Coronavirus is a species of virus belonging to the subfamily Coronavirinae in the family Coronaviridae, in the order Nidovirales. Coronaviruses are enveloped viruses with a positive-sense single-stranded RNA genome and with a nucleocapsid of helical symmetry.

In one embodiment, the coronavirus infection is an infection of the upper and/or lower respiratory tract. The "upper respiratory tract" includes the mouth, nose, sinus, middle ear, throat, larynx, and trachea. The "lower respiratory tract" includes the bronchial tubes (bronchi) and the lungs (bronchi, bronchioles and alveoli), as well as the interstitial tissue of the lungs.

In another embodiment, the coronavirus infection is an infection of the gastrointestinal tract. The "gastrointestinal tract" may include any area of the canal from the mouth to the anus, including the mouth, esophagus, stomach, and intestines.

In yet another embodiment, the coronavirus infection is a renal infection.

It is understood and herein contemplated that the coronavirus infections disclosed herein can cause a pathological state associated with the coronavirus infection referred to herein as a "coronavirus disease." In some embodiments, the coronavirus disease is selected from a common cold, pneumonia, pneumonitis, bronchitis, severe acute respiratory syndrome (SARS), coronavirus disease 2019 (COVID-2019), Middle East respiratory syndrome (MERS), sinusitis, porcine diarrhea, porcine epidemic diarrhea, avian infections bronchitis, otitis and pharyngitis. In some embodiments, the coronavirus infection is a common cold. In some embodiments, the coronavirus infection is selected from SARS, COVID-19, and MERS. In a particular embodiment, the coronavirus infection is COVID-19. In another particular embodiment, the coronavirus infection is IBV, PorCoV HKU15, or PEDV.

Most patients identified with SARS were previously healthy adults aged 25-70 years. A few suspected cases of SARS have been reported among children under 15 years. The case fatality among persons with illness meeting the current World Health Organization case definition for probable and suspected cases of SARS is around 3%.

Other indications associated with coronavirus infections are described in Gralinski & Baric, 2015, *J. Pathol.* 235: 185-195 and Cavanagh, 2005, "Coronaviridae: a review of coronavirus and toroviruses", *Coronaviruses with Special Emphasis on First Insights Concerning SARS* 1, ed. By A. Schmidt, M. H. Wolff and O. Weber, Birkhauser Verlag Baser, Switzerland, each of which is incorporated herein by reference in their entirety.

The coronavirus causing the infection may be selected from an alphacoronavirus, a betacoronavirus, a gammacoronavirus, or a deltacoronavirus.

Representative examples of alphacoronaviruses include, but are not limited to, a colacovirus (e.g., Bat coronavirus CDPHE15), a decacovirus (e.g., Bat coronavirus HKU10, Rhinolophus ferrumequinum alphacoronavirus Hub-2013), a duvinacovirus (e.g., Human coronavirus 229E), a luchacovirus (e.g., Lucheng Rn rat coronavirus), a minacovirus (e.g., Ferret coronavirus, Mink coronavirus 1), a minunacovirus (e.g., Miniopterus bat coronavirus 1, Miniopterus bat coronavirus HKU8), a myotacovirus (e.g., *Myotis rickettii* alphacoronavirus Sax-2011), a nyctacovirus (e.g., *Nyctalus velutinus* alphacoronavirus SC-2013), a pedacovirus (e.g., Porcine epidemic diarrhea virus (PEDV), Scotophilus bat coronavirus 512), a rhinacovirus (e.g., Rhinolophus bat coronavirus HKU2), a setracovirus (e.g., Human coronavirus NL63, NL63-related bat coronavirus strain BtKYNL63-9b), and a tegacovirus (e.g. Alphacoronavirus 1).

Representative examples of betacoronaviruses include, but are not limited to an embecovirus 1 (e.g., Betacoronavirus 1, Human coronavirus OC43, China *Rattus* coronavirus HKU24, Human coronavirus HKU1, Murine coronavirus), a hibecovirus (e.g., Bat Hp-betacoronavirus Zhejiang2013), a merbecovirus (e.g., Hedgehog coronavirus 1, Middle East respiratory syndrome-related coronavirus (MERS-CoV), *Pipistrellus* bat coronavirus HKU5, *Tylonycteris* bat coronavirus HKU4), a nobecovirus (e.g., *Rousettus* bat coronavirus GCCDC1, Rousettus bat coronavirus HKU9), a sarbecovirus (e.g., severe acute respiratory syndrome coronavirus (SARS-CoV), severe acute respiratory syndrome coronavirus 2 (SARS-CoV-2).

Representative examples of gammacoronaviruses include, but are not limited to, a cegacovirus (e.g., Beluga whale coronavirus SQ1) and an Igacovirus (e.g., Avian coronavirus (IBV)).

Representative examples of deltacoronaviruses include, but are not limited to, an andecovirus (e.g., Wigeon coronavirus HKU20), a buldecovirus (e.g., Bulbul coronavirus HKU11, Porcine coronavirus HKU15 (PorCoV HKU15), Munia coronavirus HKU13, White-eye coronavirus HKU16), a herdecovirus (e.g., Night heron coronavirus HKU19), and a moordecovirus (e.g., Common moorhen coronavirus HKU21).

In some embodiments, the coronavirus is a human coronavirus. Representative examples of human coronaviruses include, but are not limited to, human coronavirus 229E (HCoV-229E), human coronavirus OC43 (HCoV-OC43), human coronavirus HKU1 (HCoV-HKU1), Human coronavirus NL63 (HCoV-NL63), severe acute respiratory syndrome coronavirus (SARS-CoV), severe acute respiratory syndrome coronavirus 2 (SARS-CoV-2), and Middle East respiratory syndrome-related coronavirus (MERS-CoV).

In some embodiments, the coronavirus infection can be caused an avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV.

As used herein, "COVID-19" refers to the infectious disease caused by SARS-CoV-2 and characterized by, for example, fever, cough, respiratory symptoms, rhinorrhea, sore throat, malaise, headache, chills, repeated shaking with chills, diarrhea, new loss of smell or taste, muscle pain, or a combination thereof.

In some embodiments, the subject with a coronavirus exhibits one or more symptoms associated with mild COVID-19, moderate COVID-19, mild-to-moderate COVID-19, severe COVID-19 (e.g., critical COVID-19), or exhibits no symptoms associated with COVID-19 (asymptomatic). It should be understood that in reference to the treatment of patients with different COVID-19 disease severity, "asymptomatic" infection refers to patients diagnosed with COVID-19 by a standardized RT-PCR assay that do not present with fever, cough, respiratory symptoms, rhinorrhea, sore throat, malaise, headache, or muscle pain.

In some embodiments, the subject with a coronavirus exhibits one or more symptoms selected from dry cough, shortness of breath, and fever. In other embodiments, the subject exhibits no symptoms associated with COVID-19 but has been exposed to another subject known or suspected of having COVID-19.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

Example 1: Remdesivir Ophthalmic Drops for Prevention of Covid-19 Transmission Via Eye The Center for Diseases and Control (CDC) recommends remdesivir as therapeutic option for Patients with COVID-19. Remdesivir is an investigational intravenous drug with broad antiviral activity that inhibits viral replication through premature termination of RNA transcription and has in-vitro activity against SARS-CoV-2 and in-vitro and in-vivo activity against related betacoronaviruses (see https://www.cdc.gov/coronavirus/2019-ncov/hcp/therapeutic-options.html ("cdc.gov"); https://www.ema.europa.eu/en/documents/other/summary-compassionate-use-remdesivir-gilead_en.pdf ("ema.europa.eu"); Timothy P. Sheahan, et al., Science Translational Medicine. 9, eaa13653 (2017) ("Sheanhan, et al."); and Manli Wang, et al., Cell Research 30, 269-271 (2020) ("Wang, et al.")). It has demonstrated in vitro and in vivo activity in animal models against the viral pathogens that cause MERS (Mideast Respiratory Syndrome) and SARS (Sever Acute Respiratory Syndrome), which are coronaviruses structurally similar to SARS-CoV-2, the coronavirus that causes COVID-19 (see cdc.gov; ema.europa.eu; Sheanhan, et al.; and Wang, et al.). Several clinical trials are ongoing for potential treatment of coronavirus using remdesivir (cdc.gov). In addition, Gilead Sciences, Inc. has initiated of two Phase 3 clinical studies to evaluate the safety and efficacy of remdesivir in adults diagnosed with COVID-19 (novel coronavirus) on Feb. 26, 2020 (see cdc.gov). In in vitro cell model, remdesivir has efficiently inhibited both MERS-CoV and SARS-CoV replication with IC50 values of 0.074 and 0.069 μM, respectively in HAE cells (see Sheanhan, et al.). Remdesivir also showed in vitro activity against SARS-CoV-2 in Vero cells (EC50=0.77 μM) in another study conducted by the Wuhan Institute of Virology (see Sheanhan, et al.). One study from China suggests that up to one third of people hospitalized with coronavirus experienced viral pink eye or conjunctivitis (see ema.europa.eu). The virus can spread by touching fluid from an infected person's eyes, or from objects that carry the fluid (see https://www.aao.org/eye-health/tips-prevention/corona virus-covid19-eye-infection-pinkeye). Described herein are remdesivir ophthalmic drops that provide concentration of 0.77 μM in the eye cells. The formulation has potential for prevention of transmission of the diseases via eye and has also potential for treatment for conjunctivitis caused by the infection.

Experimental series 1: A human corneal epithelial cell line (ATCC-CRL-11515 cells) and The Wong-Kilbourne derivative of Chang conjunctival cells (ATCC CCL-20.2) will be utilized to test the eye drops. Cultured cells will be proliferated and the remdesivir eye drops will be delivered three times a day. Cells will be collected to identify for presence of remdesivir in the cells. HPLC assay will be utilized to perform the assay for detection and presence of remdesivir in cells and compared with cells treated with vehicle control.

Experimental series 2: The cytotoxicity of remdesivir eye drops will be assessed in a human corneal epithelial cell line (ATCC-CRL-11515 cells) and The Wong-Kilbourne derivative of Chang conjunctival cells (ATCC CCL-20.2) (see Ayaki M, et al., Clin Ophthalmol. 2012; 6:1879-1884). Cell viability will be determined by the 3-(4,5-dimethyl-2 thiazoyl)-2,5-diphenyl-2H-tetrazolium bromide (MTT assay) exposing the cells to remdesivir eye drops.

Experimental series 3: Spike protein has been previously identified as a key target due to its capability for interaction with ACE2 protein in the vascular cell. Based on the molecular structure currently know, the single stranded RNA SARS-Cov-2 is enveloped in glycoprotein along with the spike protein that the virus utilizes to recognize the cell surface and entry. We will utilize the purified Spike protein as a model to expose the cells and identify the increase in Nfκb changes in cells. Ocular drops for Angiotensin receptor blocker (ARB) such as losartan or telmisartan will also be prepared and tested utilizing the spike protein exposed to the both cells to identify the decreased inflammatory conditions. Overall a decrease in inflammation and cytokine release from eye cells will point to the feasibility that the protein that the virus utilizes to travel and transmit will be eliminated from eye surfaces and ocular cell contacts.

Results: The in vitro testing can identify the delivery and feasibility of remdesivir for ocular drug delivery. Ocular drug delivery can allow us to develop a model for inhibiting and/or preventing the transmission of the deadly virus along with its components. In addition to Remdesivir, testing of ARB can provide feasibility for decreased interactions of Virus particle with the ACE2 (angiotensin converting enzyme)/Angiotensin system in the vasculature. Overall, the multimodal ways of blocking the entry of virus into blood circulation and antiviral therapeutic strategies can significantly decrease the modes of transmission of Covid-19 via ocular secretions including lachrymal glands, surface contact, and plausible transmission from person-to person. The ocular drug delivery is a method of prevention and transmission of coronavirus via the eye along with treatment of conjunctivitis caused by this virus. Testing the efficacy of the formulation in coronavirus transcription model for further validation and discovery can be performed.

Example 2: Remdesivir Ophthalmic Drops for Prevention of Covid-19 Transmission Via Eye Described is an ophthalmic Solution (tear drops & Micelles) of remedsivir for prevention of Covid-19 transmission via eye and also as potential treatment for conjunctivitis caused by Covid-19 infection.

Remdesivir tear drops and nano-micelle were prepared using biodebradable MPEG-PCL (methoxypoly(ethylene glycol) poly(caprolactone).

MTT Assay was carried out to study toxicity of the formulation. Covid-19 Spike protein was exposed to the eye cells and inflammatory mediator IL-6 was measured using ELISA method. ARPE-19 cells were treated with COVID S-protein diluted solutions before administration of various remdesivir treatment.

The micelles particle size was 228 nm with zeta potential of 2.5 mV. The micelles were taken up by ARPE-19 ocular cell line by 90 minutes. MTT assay showed remdesivir tear drops and nanomcelles were not toxic to the ARPE-19 cells. Remdesivir nanomicelles (NP) reduced IL-6 secretion after Spike protein exposure comparted to control (+S), remdesivir solution and remdesivir tear drops (TD). Remdesivir tear drops and nanomicelle were successfully prepared and characterized. Further characterization needed in conjunctival cells and COVID cellular and animal model.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

What is claimed is:

1. An ophthalmological composition comprising a nanoparticle and ophthalmologically suitable carrier, wherein the nanoparticle comprises remdesivir, or a pharmaceutically acceptable salt thereof, in a concentration of about 15 wt %, and wherein the nanoparticle has an average diameter of from 200 to 250 nm, further wherein the nanoparticle comprises poly(lactic acid-co-glycolic-acid) carboxylic acid (PLGA-COOH).

2. The ophthalmological composition of claim 1, wherein the composition is in the form of eye drops.

3. The ophthalmological composition of claim 1, further comprising an angiotensin converting enzyme inhibitor (ACEI).

4. The ophthalmological composition of claim 1, further comprising an angiotensin receptor blocker (ARB).

5. The ophthalmological composition of claim 4, wherein the ARB comprises losartan, telmisartan, or any combination thereof.

6. The ophthalmological composition of claim 1, further comprising a corticosteroid.

7. The ophthalmological composition of claim 6, wherein the corticosteroid comprises dexamethasone.

8. The ophthalmological composition of claim 1, wherein the ophthalmologically suitable carrier comprises a biodegradable polymer, a lipid, or any combination thereof.

9. The ophthalmological composition of claim 8, wherein remdesivir is encapsulated or dispersed within the biodegradable polymer, a lipid, or any combination thereof.

10. The ophthalmological composition of claim 8, wherein the biodegradable polymer comprises a poly(hydroxy acid); poly(lactic acid); poly(glycolic acid); poly (lactic acid-co-glycolic acid); poly(lactic-co-glycolic acid); a polyanhydride; a polyorthoester; a polyamide; a polycarbonate; a polyalkylene; polyethylene; polypropylene; a polyalkylene glycol; poly(ethylene glycol); methoxypoly (ethylene glycol); a polyalkylene oxide; poly(ethylene oxide); a polyalkylene terephthalate; poly(ethylene terephthalate); a polyvinyl alcohol; a polyvinyl ether; a polyvinyl ester; a polyvinyl halide; poly(vinyl chloride); polyvinylpyrrolidone; a polysiloxane; a poly(vinyl acetate); a polyurethane; a co-polymer of a polyurethane; a derivativized cellulose; alkyl cellulose; a hydroxyalkyl cellulose; a cellulose ether; a cellulose ester; a nitro cellulose; methyl cellulose; ethyl cellulose; hydroxypropyl cellulose; hydroxypropyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; a polymer of acrylic acid; methacrylic acid; a copolymer of methacrylic acid; a derivative of methacrylic acid; poly (methyl methacrylate); poly(ethyl methacrylate); poly (butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); a copolymer of poly (lactide-co-caprolactone); a blend of poly(lactide-co-caprolactone); polygalactia poly-(isobutyl cyanoacrylate); poly(2-hydroxyethyl-L-glutamine); poly(caprolactone); or any combination, or copolymers thereof.

11. The ophthalmological composition of claim 8, wherein the lipid comprises fatty acids, glycerolipids, glycerophospholipids, sphingolipids, saccharolipids, polyketides, sterol lipids, prenol lipids, or any combination thereof.

12. A method of reducing the likelihood of a coronavirus infection from an eye in a subject comprising administering to the subject a therapeutically effective amount of an ophthalmological composition of claim 1 to the subject's eye.

13. The method of claim 12, wherein coronavirus infection is caused by an avian coronavirus (IBV), porcine coronavirus HKU15 (PorCoV HKU15), Porcine epidemic diarrhea virus (PEDV), HCoV-229E, HcoV-OC43, HcoV-HKU1, HcoV-NL63, SARS-CoV, SARS-CoV-2, or MERS-CoV.

14. The method of claim 12, further comprising administering a corticosteroid.

15. The method of claim 14, wherein the corticosteroid is dexamethasone.

16. A method of reducing the likelihood of conjunctivitis caused by a coronavirus infection in an eye of a subject in need thereof comprising administering to the subject's eye a therapeutically effective amount of an ophthalmological composition of claim 1.

17. The method of claim 16, wherein the coronavirus infection is caused by an avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV.

18. A method of inhibiting a coronavirus spike protein interaction with angiotensin converting enzyme II (ACE2) in the eye of a subject, the method comprising administering to a part of the eye of the subject an effective amount of an ophthalmological composition of claim 1.

* * * * *